US012324563B2

(12) United States Patent
Endo

(10) Patent No.: US 12,324,563 B2
(45) Date of Patent: Jun. 10, 2025

(54) IMAGE PROCESSING APPARATUS, PROCESSOR APPARATUS, ENDOSCOPE SYSTEM, IMAGE PROCESSING METHOD, AND PROGRAM ENABLING NOTIFICATION OF A BIOPSY CERTAINTY FACTOR

(71) Applicant: FUJIFILM Corporation, Tokyo (JP)

(72) Inventor: Maiko Endo, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 178 days.

(21) Appl. No.: 18/179,291

(22) Filed: Mar. 6, 2023

(65) Prior Publication Data

US 2023/0200626 A1    Jun. 29, 2023

Related U.S. Application Data

(63) Continuation of application No. PCT/JP2021/026536, filed on Jul. 15, 2021.

(30) Foreign Application Priority Data

Sep. 11, 2020 (JP) ................................ 2020-152970

(51) Int. Cl.
*A61B 1/00* (2006.01)
*G06T 7/00* (2017.01)
(Continued)

(52) U.S. Cl.
CPC .... *A61B 1/00055* (2013.01); *A61B 1/000094* (2022.02); *A61B 1/0005* (2013.01);
(Continued)

(58) Field of Classification Search
CPC .......... A61B 1/00055; A61B 1/000094; A61B 1/0005; G06T 7/0012; G06T 11/00;
(Continued)

(56) References Cited

U.S. PATENT DOCUMENTS

2011/0166418 A1*  7/2011  Aoyagi ............. A61B 1/00009
600/109
2012/0319006 A1   12/2012  Shida
(Continued)

FOREIGN PATENT DOCUMENTS

JP    2011-135983 A    7/2011
JP    2011-177419 A    9/2011
(Continued)

OTHER PUBLICATIONS

International Search Report issued in PCT/JP2021/026536; mailed Sep. 21, 2021.
(Continued)

*Primary Examiner* — Jin Cheng Wang
(74) *Attorney, Agent, or Firm* — Studebaker Brackett PLLC

(57) ABSTRACT

Provided are an image processing system, a processor apparatus, an endoscope system, an image processing method, and a program that enable notification of a biopsy certainty factor with which the obstruction of a user's field of view is suppressed. A medical image (38) is acquired, a region (500) of interest is detected from the medical image, a biopsy certainty factor representing certainty of a biopsy region that is a biopsy target is calculated for the region of interest, a notification image (502) is generated, the notification image being an image in which a degree of notification differs depending on the calculated biopsy certainty factor and being an image that is to be displayed so as to be superimposed on the medical image, and a display signal representing the notification image is transmitted to a display apparatus.

15 Claims, 8 Drawing Sheets

(51) Int. Cl.
  *G06T 11/00* (2006.01)
  *G06V 10/25* (2022.01)
  *G06V 20/50* (2022.01)
  *H04N 7/18* (2006.01)
  *H04N 23/50* (2023.01)

(52) U.S. Cl.
  CPC ............ *G06T 7/0012* (2013.01); *G06T 11/00* (2013.01); *G06V 10/25* (2022.01); *G06V 20/50* (2022.01); *H04N 7/183* (2013.01); *H04N 23/555* (2023.01); *G06T 2207/10068* (2013.01); *G06T 2207/30096* (2013.01); *G06T 2207/30168* (2013.01); *G06V 2201/03* (2022.01)

(58) Field of Classification Search
  CPC . G06T 2207/10068; G06T 2207/30096; G06T 2207/10081; G06T 2207/10088; G06V 20/50; G06V 10/25; G06V 2201/03; H04N 7/183; H04N 23/555
  See application file for complete search history.

(56) References Cited

U.S. PATENT DOCUMENTS

| | | | |
|---|---|---|---|
| 2012/0327205 | A1 | 12/2012 | Takahashi |
| 2015/0193929 | A1* | 7/2015 | Ikemoto .................. A61B 5/061 382/128 |
| 2018/0042468 | A1 | 2/2018 | Teramura |
| 2020/0043172 | A1* | 2/2020 | Ito ......................... G06T 7/0014 |
| 2020/0053296 | A1 | 2/2020 | Endo |
| 2020/0337537 | A1* | 10/2020 | Hirasawa ......... A61B 1/000096 |
| 2020/0345292 | A1* | 11/2020 | Stavros ................ A61B 8/0825 |
| 2021/0149182 | A1* | 5/2021 | Hayami ................ A61B 1/045 |
| 2021/0161506 | A1* | 6/2021 | Ito ........................... A61B 8/429 |
| 2021/0201486 | A1 | 7/2021 | Takenouchi |
| 2021/0233648 | A1 | 7/2021 | Kamon |
| 2021/0241886 | A1* | 8/2021 | Noguchi ................... G06T 7/62 |
| 2021/0274999 | A1* | 9/2021 | Kubota .............. A61B 1/00045 |
| 2021/0393109 | A1* | 12/2021 | Iketani ............. A61B 1/000094 |
| 2022/0000351 | A1* | 1/2022 | Yamada ................. G16H 30/40 |
| 2022/0028064 | A1* | 1/2022 | Wimberger-Friedl ...................... G06T 7/0012 |
| 2022/0336071 | A1* | 10/2022 | Laugerette ............. G16H 30/20 |
| 2023/0103969 | A1* | 4/2023 | St. Pierre .............. G06T 7/0014 382/128 |
| 2023/0105799 | A1* | 4/2023 | Nishide .................. G16H 40/67 382/131 |

FOREIGN PATENT DOCUMENTS

| | | |
|---|---|---|
| JP | 2013-119019 A | 6/2013 |
| JP | 2020-024286 A | 2/2020 |
| WO | 2016/175084 A1 | 11/2016 |
| WO | 2020/067105 A1 | 4/2020 |
| WO | 2020/090729 A1 | 5/2020 |

OTHER PUBLICATIONS

International Preliminary Report On Patentability and Written Opinion issued in PCT/JP2021/026536; issued Mar. 7, 2023.

An Office Action; "Notice of Reasons for Refusal," mailed by the Japanese Patent Office on Jun. 18, 2024, which corresponds to Japanese Patent Application No. 2022-547419 and is related to U.S. Appl. No. 18/179,291; with English language translation.

* cited by examiner

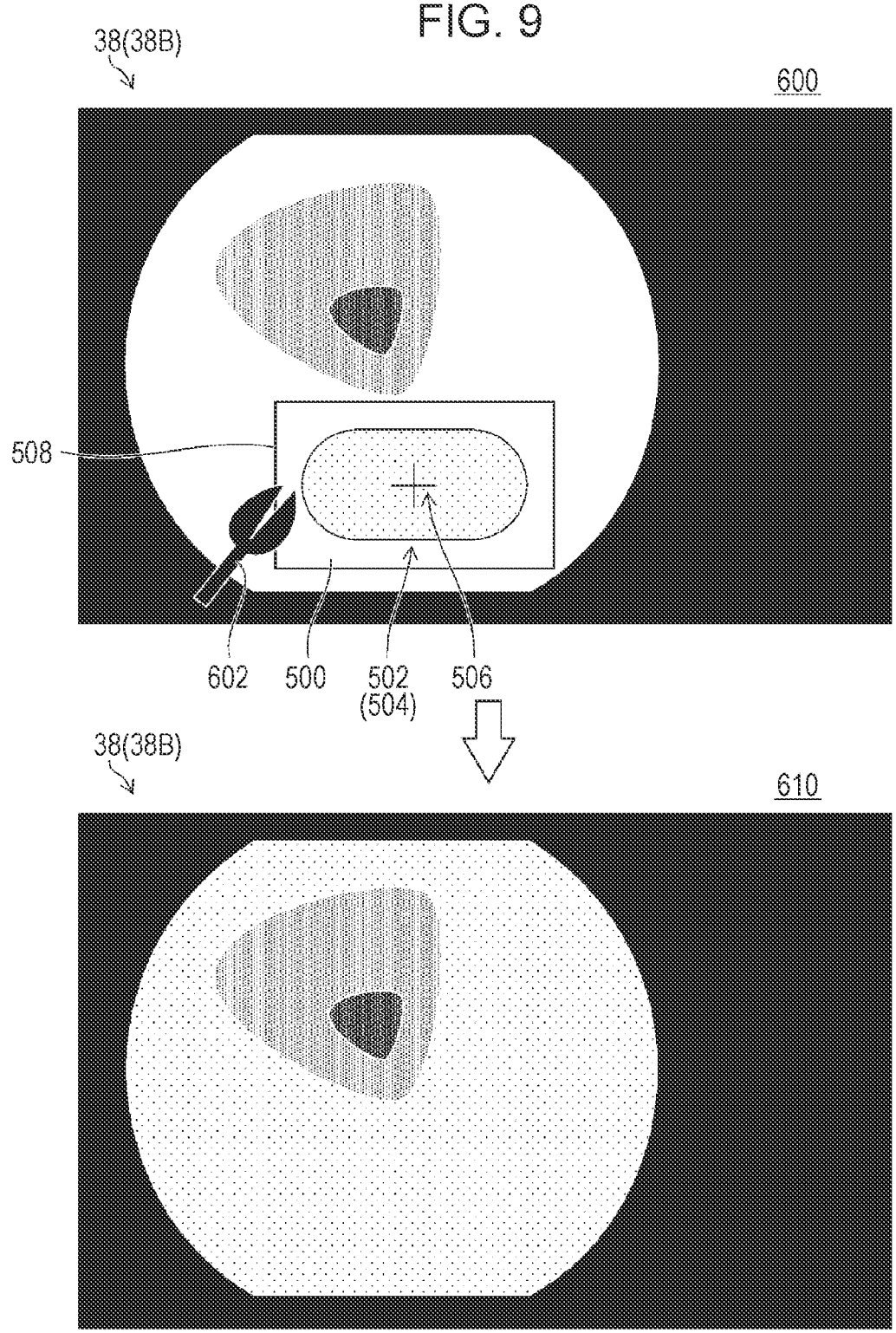

IMAGE PROCESSING APPARATUS, PROCESSOR APPARATUS, ENDOSCOPE SYSTEM, IMAGE PROCESSING METHOD, AND PROGRAM ENABLING NOTIFICATION OF A BIOPSY CERTAINTY FACTOR

CROSS-REFERENCE TO RELATED APPLICATIONS

The present application is a Continuation of PCT International Application No. PCT/JP2021/026536 filed on Jul. 15, 2021 claiming priority under 35 U.S.C § 119(a) to Japanese Patent Application No. 2020-152970 filed on Sep. 11, 2020. Each of the above applications is hereby expressly incorporated by reference, in its entirety, into the present application.

BACKGROUND OF THE INVENTION

1. Field of the Invention

The present invention relates to an image processing apparatus, a processor apparatus, an endoscope system, an image processing method, and a program.

2. Description of the Related Art

There is known a diagnosis support system that automatically recognizes a region suspected to be a lesion from a medical image such as an endoscopic image by applying image recognition processing, emphasizes the region suspected to be a lesion, and displays a recognition result on a display apparatus.

JP2011-135983A describes an endoscope system for acquiring normal-light images and special-light images. The system described in JP2011-135983A acquires a white-light image corresponding to a wavelength range of white light and a special-light image corresponding to a specific wavelength range, determines a type of a subject image included in the special-light image, and performs emphasis processing on the white-light image based on the determined type of the subject.

JP2013-119019A describes a visual performance assessment apparatus for assessing the visual performance of a subject's eyes. When displaying an acquired oxygen saturation distribution, the apparatus described in JP2013-119019A displays contour lines indicating regions with equal degrees of saturation in a superimposed manner.

SUMMARY OF THE INVENTION

However, since a region suspected to be a lesion is subjected to biopsy and a definite diagnosis is made, it is important to notify a user, such as a doctor, of the automatic recognition result. However, there is a concern that the notified automatic recognition result interferes with the field of view of the doctor or the like at the time of biopsy.

The system described in JP2011-135983A does not take into account the aspect of not obstructing the user's field of view. The same is true for the apparatus described in JP2013-119019A.

The above-described problem is not limited to the notification of the automatic recognition result in an endoscopic image, and the same problem also exists in the notification of the automatic recognition result in a medical image such as a CT image, an MRI image, and an ultrasound image.

The present invention has been made in view of such circumstances, and an object thereof is to provide an image processing system, a processor apparatus, an endoscope system, an image processing method, and a program that enable notification of a biopsy certainty factor with which the obstruction of a user's field of view is suppressed.

In order to achieve the above object, the following aspects of the invention are provided.

An image processing system according to an aspect of the present disclosure is an image processing system including one or more processors, the one or more processors being configured to: acquire a medical image; detect a region of interest from the medical image; calculate a biopsy certainty factor for the region of interest, the biopsy certainty factor representing certainty of a biopsy region that is a biopsy target; generate a notification image in which a degree of notification differs depending on the calculated biopsy certainty factor, the notification image being to be displayed so as to be superimposed on the medical image; and transmit a display signal representing the notification image to a display apparatus.

According to the image processing system according to this aspect of the present disclosure, the notification image in which the degree of notification differs depending on the biopsy certainty factor, the notification image being to be displayed so as to be superimposed on the medical image, is generated. Accordingly, notification according to the biopsy certainty factor may be performed, and the region with a reduced degree of notification in the notification image may suppress the obstruction of the field of view of the user, such as a doctor.

In an image processing system according to another aspect, the one or more processors are configured to set a threshold value for the biopsy certainty factor, and cause a biopsy certainty factor exceeding the threshold value to be displayed as the notification image.

According to this aspect, the biopsy certainty factor exceeding the prescribed threshold value may be notified as the notification image.

In an image processing system according to another aspect, the one or more processors are configured to generate the notification image in which an image quality of the notification image differs depending on the calculated biopsy certainty factor.

According to this aspect, the image quality may be applied as the degree of notification in the notification image.

In an image processing system according to another aspect, the one or more processors are configured to generate the notification image in which the image quality of a region in which the biopsy certainty factor is relatively small is reduced compared to a region in which the biopsy certainty factor is relatively large.

According to this aspect, the visibility of the medical image in the region in which the biopsy certainty factor is relatively high may be improved.

In an image processing system according to another aspect, the one or more processors are configured to generate the notification image in which a saturation of the notification image differs depending on the calculated biopsy certainty factor.

According to this aspect, the saturation may be applied as the degree of notification in the notification image.

In an image processing system according to another aspect, the one or more processors are configured to generate the notification image in which the saturation of a region in which the biopsy certainty factor is relatively small is reduced compared to a region in which the biopsy certainty factor is relatively large.

According to this aspect, the visibility of the medical image in the region in which the biopsy certainty factor is relatively high may be improved.

In an image processing system according to another aspect, the one or more processors are configured to generate the notification image in which a luminance of the notification image differs depending on the calculated biopsy certainty factor.

According to this aspect, the luminance may be applied as the degree of notification in the notification image.

In an image processing system according to another aspect, the one or more processors are configured to generate the notification image in which the luminance of a region in which the biopsy certainty factor is relatively small is reduced compared to a region in which the biopsy certainty factor is relatively large.

According to this aspect, the visibility of the medical image in the region in which the biopsy certainty factor is relatively high may be improved.

In an image processing system according to another aspect, the one or more processors are configured to measure an elapsed period from a display start timing of the notification image, and stop transmission of the display signal representing the notification image if the elapsed period from the display start timing of the notification image exceeds a prescribed period.

According to this aspect, the notification image may be hidden. Accordingly, the notification image does not obstruct the user's visual recognition.

In an image processing system according to another aspect, the one or more processors are configured to detect whether a biopsy has been performed, and stop transmission of the display signal representing the notification image if a detection result indicating that the biopsy has been performed is obtained.

According to this aspect, the notification image may be hidden in response to the execution of the biopsy. Accordingly, the notification image does not obstruct the user's visual recognition.

In an image processing system according to another aspect, the one or more processors are configured to calculate a lesion certainty factor for the region of interest, the lesion certainty factor representing certainty of a lesion, and calculate the biopsy certainty factor for the region of interest in which the lesion certainty factor exceeds a prescribed threshold value.

According to this aspect, it is possible to derive the biopsy certainty factor according to the certainty of a lesion.

A processor apparatus according to an aspect of the present disclosure is a processor apparatus for controlling an endoscope, including one or more processors, the one or more processors being configured to: acquire an endoscopic image from the endoscope; detect a region of interest from the endoscopic image; calculate a biopsy certainty factor for the region of interest, the biopsy certainty factor representing certainty of a biopsy region that is a biopsy target; generate a notification image in which a degree of notification differs depending on the calculated biopsy certainty factor, the notification image being to be displayed so as to be superimposed on the endoscopic image; and transmit a display signal representing the notification image to a display apparatus.

According to the processor apparatus according to this aspect of the present disclosure, it is possible to obtain the same advantageous effects as those of the image processing system according to any of the above aspects of the present disclosure. The processor apparatus according to this aspect of the present disclosure may employ the components of the image processing system according to any of the above aspects of the present disclosure.

An endoscope system according to an aspect of the present disclosure is an endoscope system including: an endoscope; a processor apparatus for controlling the endoscope; and one or more processors, the one or more processors being configured to: acquire an endoscopic image from the endoscope; detect a region of interest from the endoscopic image; calculate a biopsy certainty factor for the region of interest, the biopsy certainty factor representing certainty of a biopsy region that is a biopsy target; generate a notification image in which a degree of notification differs depending on the calculated biopsy certainty factor, the notification image being to be displayed so as to be superimposed on the endoscopic image; and transmit a display signal representing the notification image to a display apparatus.

According to the endoscope system according to this aspect of the present disclosure, it is possible to obtain the same advantageous effects as those of the image processing system according to any of the above aspects of the present disclosure. The endoscope system according to this aspect of the present disclosure may employ the components of the image processing system according to any of the above aspects of the present disclosure.

An image processing method according to an aspect of the present disclosure is an image processing method including: acquiring a medical image; detecting a region of interest from the medical image; calculating a biopsy certainty factor for the region of interest, the biopsy certainty factor representing certainty of a biopsy region that is a biopsy target; generating a notification image in which a degree of notification differs depending on the calculated biopsy certainty factor, the notification image being to be displayed so as to be superimposed on the medical image; and transmitting a display signal representing the notification image to a display apparatus.

According to the image processing method according to this aspect of the present disclosure, it is possible to obtain the same advantageous effects as those of the image processing system according to any of the above aspects of the present disclosure. The image processing method according to this aspect of the present disclosure may employ the components of the image processing system according to any of the above aspects of the present disclosure.

A program according to an aspect of the present disclosure is a program for causing a computer to implement: a function of acquiring a medical image; a function of detecting a region of interest from the medical image; a function of calculating a biopsy certainty factor for the region of interest, the biopsy certainty factor representing certainty of a biopsy region that is a biopsy target; a function of generating a notification image in which a degree of notification differs depending on the calculated biopsy certainty factor, the notification image being to be displayed so as to be superimposed on the medical image; and a function of transmitting a display signal representing the notification image to a display apparatus.

According to the program according to this aspect of the present disclosure, it is possible to obtain the same advantageous effects as those of the image processing system according to any of the above aspects of the present disclosure. The program according to this aspect of the present disclosure may employ the components of the image processing system according to any of the above aspects of the present disclosure.

According to the present invention, the notification image in which the degree of notification differs depending on the biopsy certainty factor is generated. Accordingly, notification according to the biopsy certainty factor may be performed, and the region with a reduced degree of notification in the notification image may suppress the obstruction of the field of view of the user, such as a doctor.

BRIEF DESCRIPTION OF THE DRAWINGS

FIG. 9 is a schematic diagram of transition of a notification image.

DESCRIPTION OF THE PREFERRED EMBODIMENTS

Figure 1:
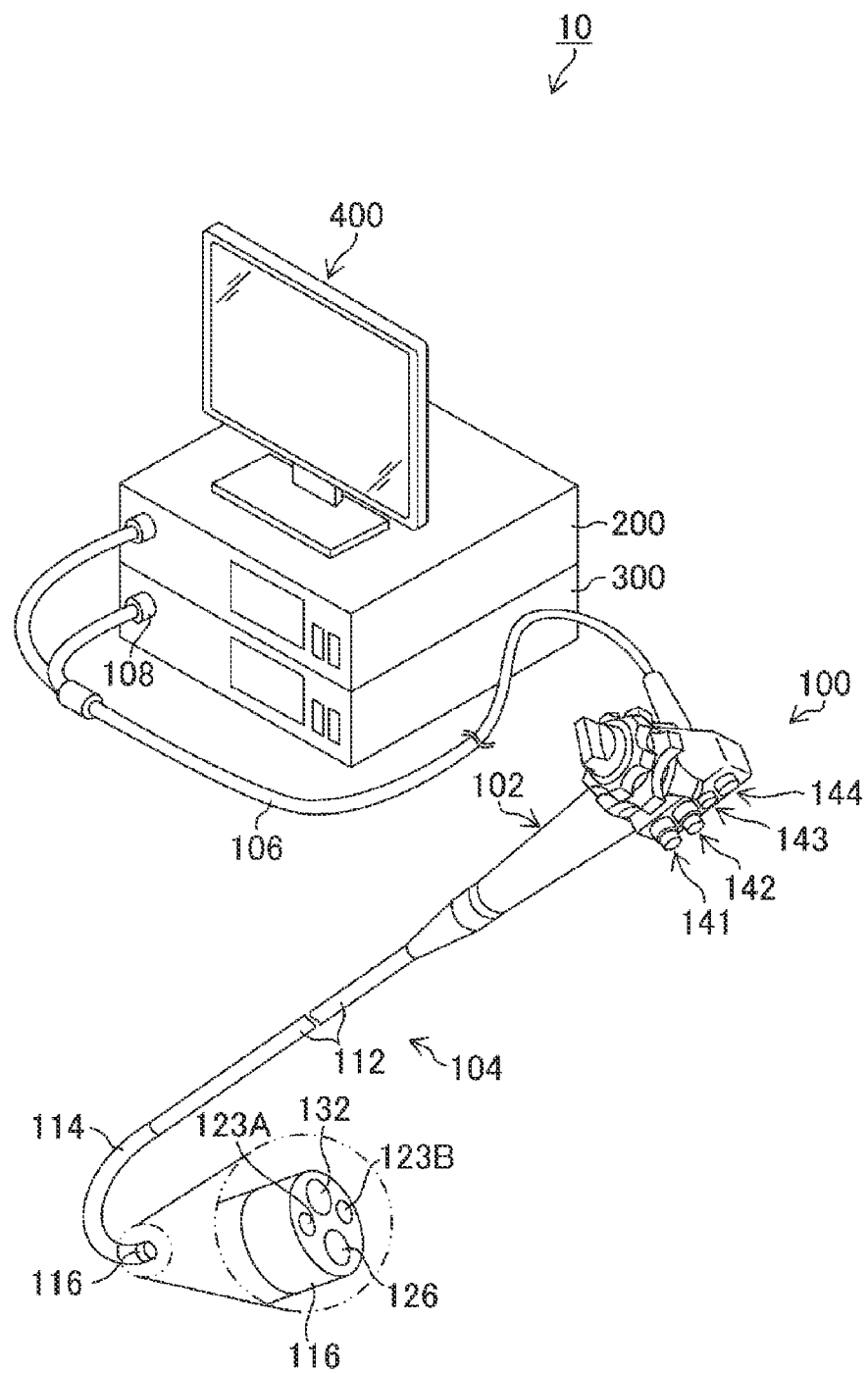
FIG. 1 is an overall configuration diagram of an endoscope system according to a first embodiment.

Hereinafter, preferred embodiments of the present invention will be described in detail with reference to the accompanying drawings. In the present specification, the same components are denoted by the same reference numerals, and overlapping description will be appropriately omitted.

Endoscope System According to First Embodiment

Overall Configuration of Endoscope System

FIG. 1 is an overall configuration diagram of an endoscope system according to a first embodiment. An endoscope system 10 includes an endoscope main body 100, a processor apparatus 200, a light source device 300, and a display apparatus 400. In this figure, a part of a tip rigid part 116 provided in the endoscope main body 100 is enlarged.

Configuration Example of Endoscope Main Body

The endoscope main body 100 includes a hand operating unit 102 and an insertion unit 104. A user grips and operates the hand operating unit 102, inserts the insertion unit 104 into a subject's body, and observes the inside of the subject's body. Note that the user is synonymous with a doctor, an operator, and the like. The subject as used herein is synonymous with a patient and an examinee.

The hand operating unit 102 includes an air/water supply button 141, a suction button 142, a function button 143, and an imaging button 144. The air/water supply button 141 receives an operation of an air supply instruction and a water supply instruction.

The suction button 142 receives a suction instruction. Various functions are assigned to the function button 143. The function button 143 receives instructions of various functions. The imaging button 144 receives an imaging instruction operation. Imaging includes capturing a moving image and capturing a still image.

The insertion unit 104 includes a soft part 112, a bending part 114, and the tip rigid part 116. The soft part 112, the bending part 114, and the tip rigid part 116 are arranged in the order of the soft part 112, the bending part 114, and the tip rigid part 116 from the hand operating unit 102 side. That is, the bending part 114 is connected to the proximal end side of the tip rigid part 116, the soft part 112 is connected to the proximal end side of the bending part 114, and the hand operating unit 102 is connected to the proximal end side of the insertion unit 104.

The user can bend the bending part 114 by operating the hand operating unit 102 to change the direction of the tip rigid part 116 vertically and horizontally. The tip rigid part 116 includes an imaging unit, an illumination unit, and a forceps port 126.

FIG. 1 illustrates an imaging lens 132 constituting the imaging unit. FIG. 1 further illustrates an illumination lens 123A and an illumination lens 123B constituting the illumination unit. Note that the imaging unit is illustrated and denoted by reference numeral 130 in FIG. 2. In addition, the illumination unit is illustrated and denoted by reference numeral 123 in FIG. 2.

Figure 2:
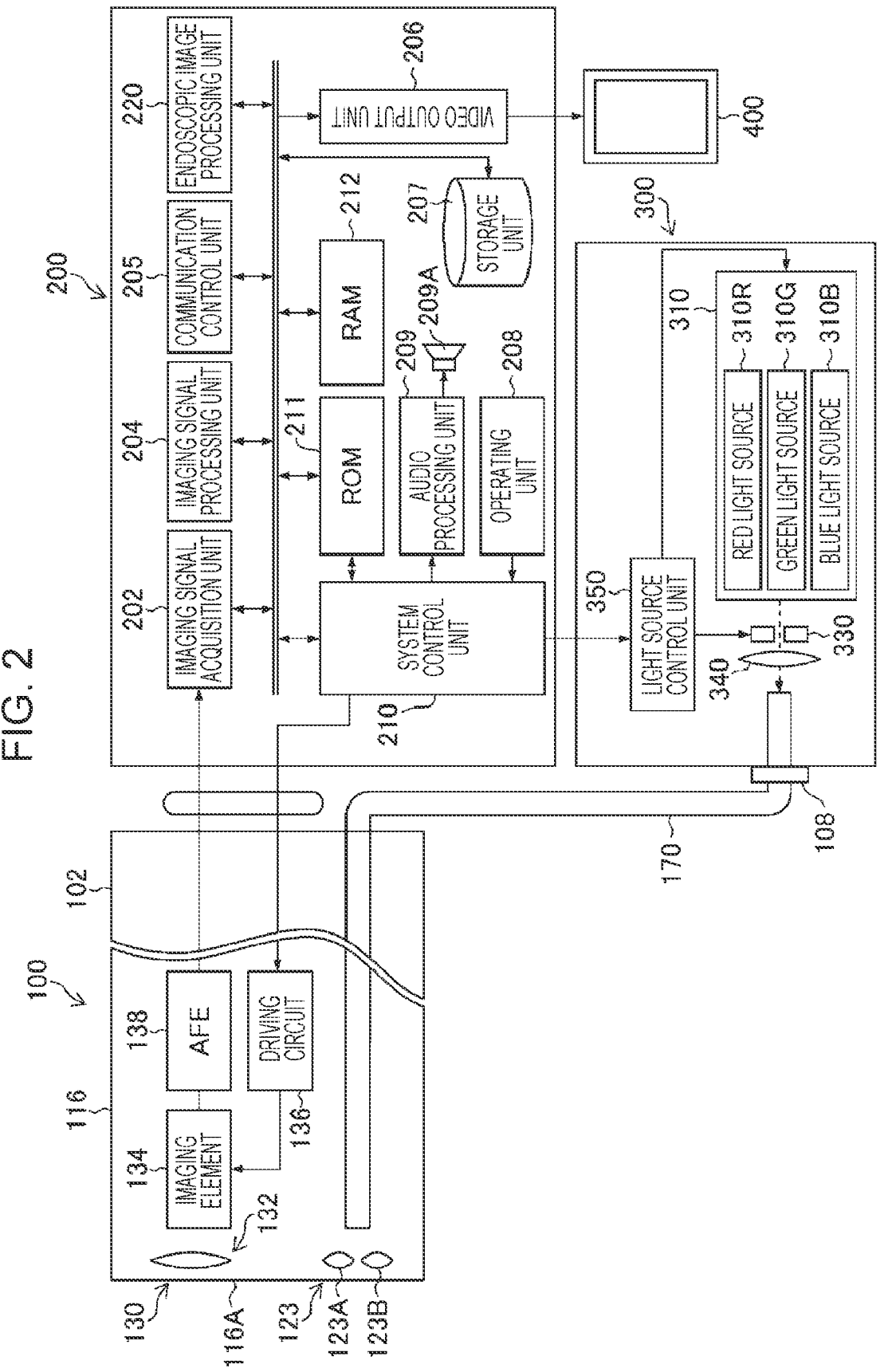
FIG. 2 is a functional block diagram of the endoscope system illustrated in FIG. 1.

At the time of observation and treatment, at least one of white light or narrow-band light is output via the illumination lens 123A and the illumination lens 123B in accordance with the operation of an operating unit 208 illustrated in FIG. 2.

Upon the air/water supply button 141 being operated, cleaning water is discharged from a water supply nozzle, or gas is discharged from an air supply nozzle. The cleaning water and gas are used for cleaning the illumination lens 123A and the like. Note that illustration of the water supply nozzle and the air supply nozzle is omitted. The water supply nozzle and the air supply nozzle may be made common.

The forceps port 126 communicates with a pipe line. A treatment tool is inserted into the pipe line. The treatment tool is supported so as to be able to advance and retreat as appropriate. At the time of removal of a tumor or the like, a necessary treatment is performed by applying the treatment tool. Note that reference numeral 106 illustrated in FIG. 1 denotes a universal cable. Reference numeral 108 denotes a light guide connector.

FIG. 2 is a functional block diagram of the endoscope system. The endoscope main body 100 includes the imaging unit 130. The imaging unit 130 is disposed inside the tip rigid part 116. The imaging unit 130 includes the imaging lens 132, an imaging element 134, a driving circuit 136, and an analog front end 138.

The imaging lens 132 is disposed on a distal-end-side end surface 116A of the tip rigid part 116. The imaging element 134 is disposed at a position opposite to the distal-end-side end surface 116A of the imaging lens 132. A CMOS image sensor is applied to the imaging element 134. A CCD image sensor may also be applied to the imaging element 134. Note that CMOS is an abbreviation for Complementary Metal-Oxide Semiconductor. CCD is an abbreviation for Charge Coupled Device.

A color imaging element is applied to the imaging element 134. An example of the color imaging element is an imaging element including color filters corresponding to RGB. Note that RGB is initial letters of red, green, and blue.

A monochrome imaging element may also be applied to the imaging element 134. If a monochrome imaging element is applied to the imaging element 134, the imaging unit 130 can perform frame-sequential or color-sequential imaging by switching the wavelength range of an incidence ray of the imaging element 134.

The driving circuit 136 supplies various timing signals necessary for the operation of the imaging element 134 to the imaging element 134 based on a control signal transmitted from the processor apparatus 200.

The analog front end 138 includes an amplifier, a filter, and an AD converter. Note that AD is initial letters of analog and digital. The analog front end 138 performs processing such as amplification, noise removal, and analog-to-digital conversion on an output signal of the imaging element 134. The output signal of the analog front end 138 is transmitted to the processor apparatus 200. Note that AFE illustrated in FIG. 2 is an abbreviation for Analog Front End.

An optical image of an observation target is formed on a light receiving surface of the imaging element 134 via the imaging lens 132. The imaging element 134 converts the optical image of the observation target into an electric signal. The electric signal output from the imaging element 134 is transmitted to the processor apparatus 200 via a signal line.

The illumination unit 123 is disposed in the tip rigid part 116. The illumination unit 123 includes the illumination lens 123A and the illumination lens 123B. The illumination lens 123A and the illumination lens 123B are arranged at positions adjacent to the imaging lens 132 on the distal-end-side end surface 116A.

The illumination unit 123 includes a light guide 170. An exit end of the light guide 170 is disposed at a position opposite to the distal-end-side end surface 116A of the illumination lens 123A and the illumination lens 123B.

The light guide 170 is inserted into the insertion unit 104, the hand operating unit 102, and the universal cable 106 illustrated in FIG. 1. An incident end of the light guide 170 is disposed inside the light guide connector 108.

Configuration Example of Processor Apparatus

The processor apparatus 200 includes an imaging signal acquisition unit 202, an imaging signal processing unit 204, a communication control unit 205, and a video output unit 206. The imaging signal acquisition unit 202 acquires an electric signal corresponding to an optical image of an observation target transmitted from the endoscope main body 100.

The imaging signal processing unit 204 generates an endoscopic image of the observation target based on an imaging signal, which is an electric signal corresponding to the optical image of the observation target. Note that the endoscopic image is illustrated and denoted by reference numeral 38 in FIG. 3.

The imaging signal processing unit 204 can perform image quality correction by applying digital signal processing such as white balance processing and shading correction processing to the imaging signal. The imaging signal processing unit 204 may add accessory information defined by the DICOM standard to the endoscopic image. Note that DICOM is an abbreviation for Digital Imaging and Communication in Medicine.

The video output unit 206 transmits a display signal representing an image generated using the imaging signal processing unit 204 to the display apparatus 400. The display apparatus 400 displays the image of the observation target.

Upon the imaging button 144 illustrated in FIG. 1 being operated, the processor apparatus 200 causes the imaging signal acquisition unit 202, the imaging signal processing unit 204, and the like to operate in accordance with an imaging command signal transmitted from the endoscope main body 100.

Upon acquiring a freeze command signal representing still image capturing from the endoscope main body 100, the processor apparatus 200 applies the imaging signal processing unit 204 to generate a still image based on a frame image at the operation timing of the imaging button 144. The processor apparatus 200 causes the display apparatus 400 to display the still image. Note that the frame image is denoted by reference numeral 38B in FIG. 3. The still image is denoted by reference numeral 39 in FIG. 3.

The processor apparatus 200 includes the communication control unit 205. The communication control unit 205 controls communication with an apparatus communicably connected via an in-hospital system, an in-hospital LAN, or the like. The communication control unit 205 can apply a communication protocol conforming to the DICOM standard. Note that an example of the in-hospital system is a hospital information system (HIS). LAN is an abbreviation for Local Area Network.

The processor apparatus 200 includes a storage unit 207. The storage unit 207 stores an endoscopic image generated using the endoscope main body 100. The storage unit 207 may store various kinds of information accompanying the endoscopic image.

The processor apparatus 200 includes the operating unit 208. The operating unit 208 outputs a command signal corresponding to an operation by a user. A keyboard, a mouse, a joystick, or the like is applicable as the operating unit 208.

The processor apparatus 200 includes an audio processing unit 209 and a speaker 209A. The audio processing unit 209 generates an audio signal representing information to be notified as audio. The speaker 209A converts the audio signal generated using the audio processing unit 209 into audio. Examples of the audio output from the speaker 209A include a message, voice guidance, and a warning sound.

The processor apparatus 200 includes a system control unit 210, a ROM 211, and a RAM 212. Note that ROM is an abbreviation for Read Only Memory. RAM is an abbreviation for Random Access Memory.

The system control unit 210 functions as an overall control unit of the processor apparatus 200. The system control unit 210 functions as a memory controller that controls the ROM 211 and the RAM 212. The ROM 211 stores various programs, control parameters, and the like applied to the processor apparatus 200.

The RAM 212 is applied to a temporary data storage area for various kinds of processing and a processing area for arithmetic processing using the system control unit 210. The RAM 212 can be applied to a buffer memory when an endoscopic image is acquired.

The processor apparatus 200 performs various kinds of processing on an endoscopic image generated using the endoscope main body 100, and causes the display apparatus 400 to display the endoscopic image and various kinds of information accompanying the endoscopic image. The processor apparatus 200 stores the endoscopic image and various kinds of information accompanying the endoscopic image.

That is, in an endoscopic examination using the endoscope main body 100, the processor apparatus 200 displays an endoscopic image and the like using the display apparatus 400, outputs audio information using the speaker 209A, and performs various kinds of processing on the endoscopic image.

The processor apparatus 200 includes an endoscopic image processing unit 220. The endoscopic image processing unit 220 performs various kinds of image processing on an endoscopic image generated using the imaging signal processing unit 204. Hardware Configuration of Processor Apparatus A computer is applicable as the processor apparatus 200. The computer can implement the functions of the processor apparatus 200 by applying the following hardware and executing a prescribed program. Note that the program is synonymous with software.

In the processor apparatus 200, various processor devices can be applied as a signal processing unit that performs signal processing. Examples of the processor device include a CPU and a GPU (Graphics Processing Unit). The CPU is a general-purpose processor device that executes a program and functions as a signal processing unit. The GPU is a processor device specialized in image processing. As hardware of the processor device, an electric circuit in which electric circuit elements such as semiconductor elements are combined is applied. Each control unit includes a ROM in which a program or the like is stored and a RAM which is a work area or the like for various calculations.

Two or more processor devices may be applied to one signal processing unit. Two or more processor devices may be processor devices of the same type or processor devices of different types. Furthermore, one processor device may be applied to a plurality of signal processing units. Note that the processor apparatus 200 described in the embodiment corresponds to an example of an endoscope control unit.

Configuration Example of Light Source Device

The light source device 300 includes a light source 310, an aperture diaphragm 330, a condenser lens 340, and a light source control unit 350. The light source device 300 causes observation light to enter the light guide 170. The light source 310 includes a red light source 310R, a green light source 310G, and a blue light source 310B. The red light source 310R, the green light source 310G, and the blue light source 310B emit red narrow-range light, green narrow-range light, and blue narrow-range light, respectively.

The light source 310 may generate illumination light that is any combination of red narrow-range light, green narrow-range light, and blue narrow-range light. For example, the light source 310 may generate white light by combining red narrow-range light, green narrow-range light, and blue narrow-range light. In addition, the light source 310 may generate narrow-range light by combining any two of red narrow-range light, green narrow-range light, and blue narrow-range light.

The light source 310 can generate narrow-range light by using any one of red narrow-range light, green narrow-range light, and blue narrow-range light. The light source 310 may selectively switch and emit white light or narrow-range light. Note that the narrow-band light is synonymous with special light. The light source 310 may include an infrared light source that emits infrared light, an ultraviolet light source that emits ultraviolet light, and the like.

The light source 310 may employ a configuration including a white light source that emits white light, a filter that transmits white light, and a filter that transmits narrow-range light. The light source 310 with such a configuration can selectively emit either white light or narrow-range light by switching between the filter that transmits white light and the filter that transmits narrow-range light.

The filter that transmits narrow-range light may include a plurality of filters corresponding to different ranges. The light source 310 may selectively switch between the plurality of filters corresponding to different ranges to selectively emit a plurality of kinds of narrow-range light.

The light source 310 may apply a type, a wavelength range, and the like in accordance with a type of an observation target, an observation purpose, and the like. Examples of the type of the light source 310 include a laser light source, a xenon light source, an LED light source, and the like. Note that LED is an abbreviation for Light-Emitting Diode.

When the light guide connector 108 is connected to the light source device 300, the observation light emitted from the light source 310 reaches the incident end of the light guide 170 via the aperture diaphragm 330 and the condenser lens 340. The observation light is emitted to the observation target via the light guide 170, the illumination lens 123A, and the like.

The light source control unit 350 transmits a control signal to the light source 310 and the aperture diaphragm 330 based on a command signal transmitted from the processor apparatus 200. The light source control unit 350 controls the illuminance of the observation light emitted from the light source 310, switching of the observation light, on/off of the observation light, and the like.

Configuration Example of Endoscopic Image Processing Unit

Figure 3:
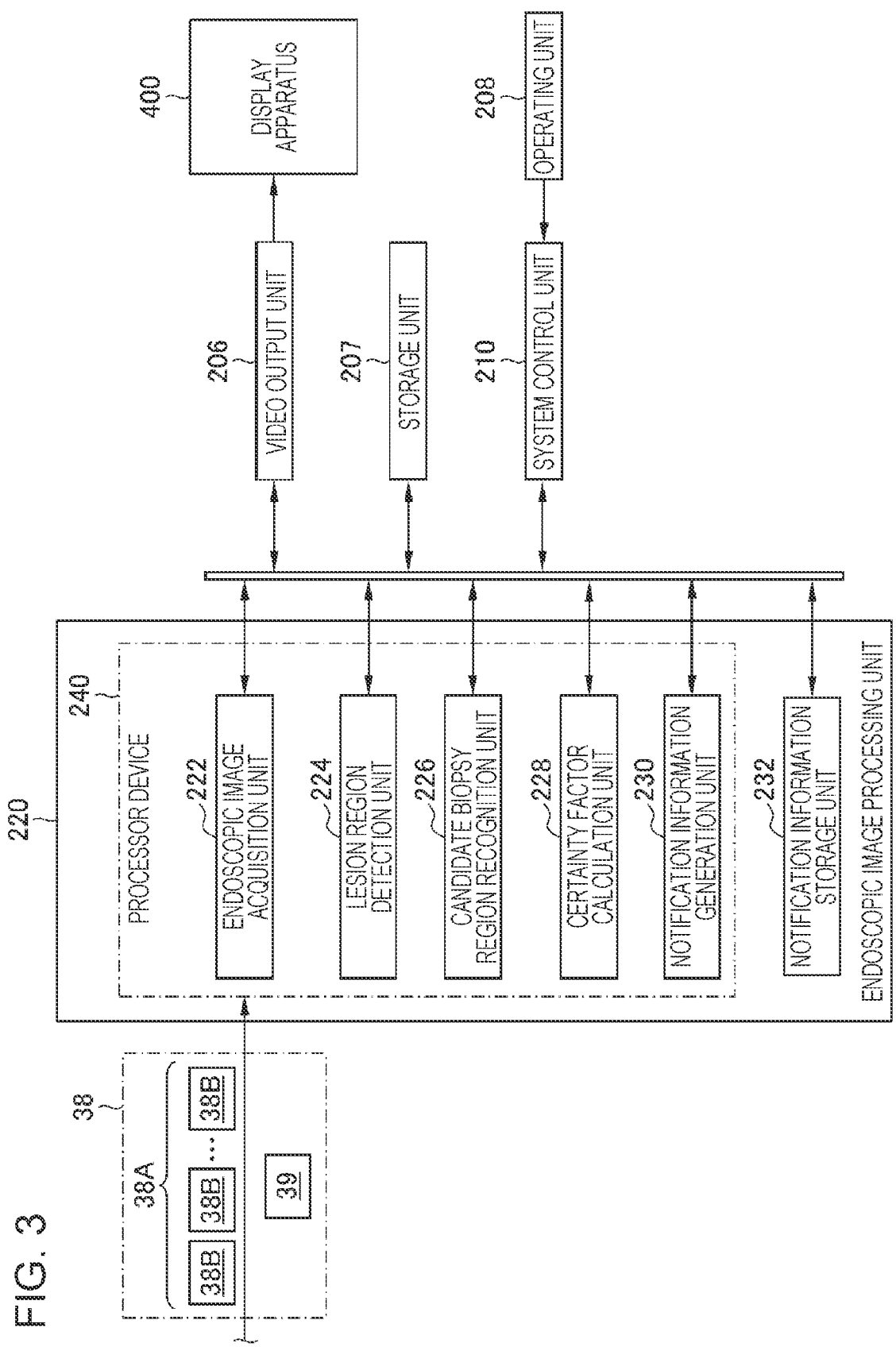
FIG. 3 is a block diagram of an endoscopic image processing unit illustrated in FIG. 1.

FIG. 3 is a block diagram of the endoscopic image processing unit illustrated in FIG. 1. For convenience of description, FIG. 3 illustrates some of the components of the processor apparatus 200 illustrated in FIG. 2.

The endoscopic image processing unit 220 includes a processor device 240. The processor device 240 includes functions as an endoscopic image acquisition unit 222, a lesion region detection unit 224, a candidate biopsy region recognition unit 226, a certainty factor calculation unit 228, and a notification information generation unit 230. The endoscopic image processing unit 220 includes a notification information storage unit 232. Note that the processor device 240 described in the embodiment is an example of one or more processors.

The endoscopic image acquisition unit 222 acquires the endoscopic image 38 captured using the endoscope main body 100 illustrated in FIG. 1. Hereinafter, the acquisition of the endoscopic image 38 may include acquisition of a moving image 38A, acquisition of the frame image 38B, and acquisition of the still image 39.

The endoscopic image acquisition unit 222 may acquire the moving image 38A composed of time-series frame images 38B. The endoscopic image acquisition unit 222 may acquire the still image 39 if still image capturing is performed in the middle of capturing of the moving image 38A. The endoscopic image acquisition unit 222 stores the acquired endoscopic image 38. The RAM 212 is applicable for storage of the endoscopic image 38.

The lesion region detection unit 224 automatically detects a lesion region, which is a region suspected to be a lesion, as a region of interest from each of the frame images 38B constituting the moving image 38A or the still image 39. The lesion region detection unit 224 stores information on the detected lesion region in association with the frame image 38B or the still image 39. The RAM 212 is applicable for storage of the information on the lesion region.

The information on the lesion region may include information on the position of the lesion region. Examples of lesions include a tumor, a polyp, an ulcer, inflammation, and the like. The lesion region detection unit 224 may apply a method based on known image processing. The lesion region detection unit 224 may apply a trained learning model.

The candidate biopsy region recognition unit 226 recognizes a candidate biopsy region that is a candidate for a biopsy region, which is a region to be biopsied, for the lesion region detected from the endoscopic image 38 using the lesion region detection unit 224. If a plurality of lesion regions are detected, a candidate biopsy region is recognized for each lesion region. If the lesion region has a prescribed area or more, the candidate biopsy region may be recognized.

The certainty factor calculation unit 228 calculates a biopsy certainty factor representing the certainty of the candidate biopsy region as a biopsy region. The certainty factor calculation unit 228 may calculate the biopsy certainty factor as a score and a probability for each of pixels constituting the candidate biopsy region.

The notification information generation unit 230 generates notification information for notifying the biopsy certainty factor. An example of the notification information is a notification image displayed so as to be superimposed on an endoscopic image displayed on the display apparatus 400. The notification information generation unit 230 generates a notification image in which the degree of notification differs depending on the biopsy certainty factor.

The notification information storage unit 232 stores the notification information including the notification image. The notification information storage unit 232 may store the notification information in association with the information on the lesion region and the information on the candidate biopsy region.

Procedure of Image Processing Method According to First Embodiment

Figure 4:
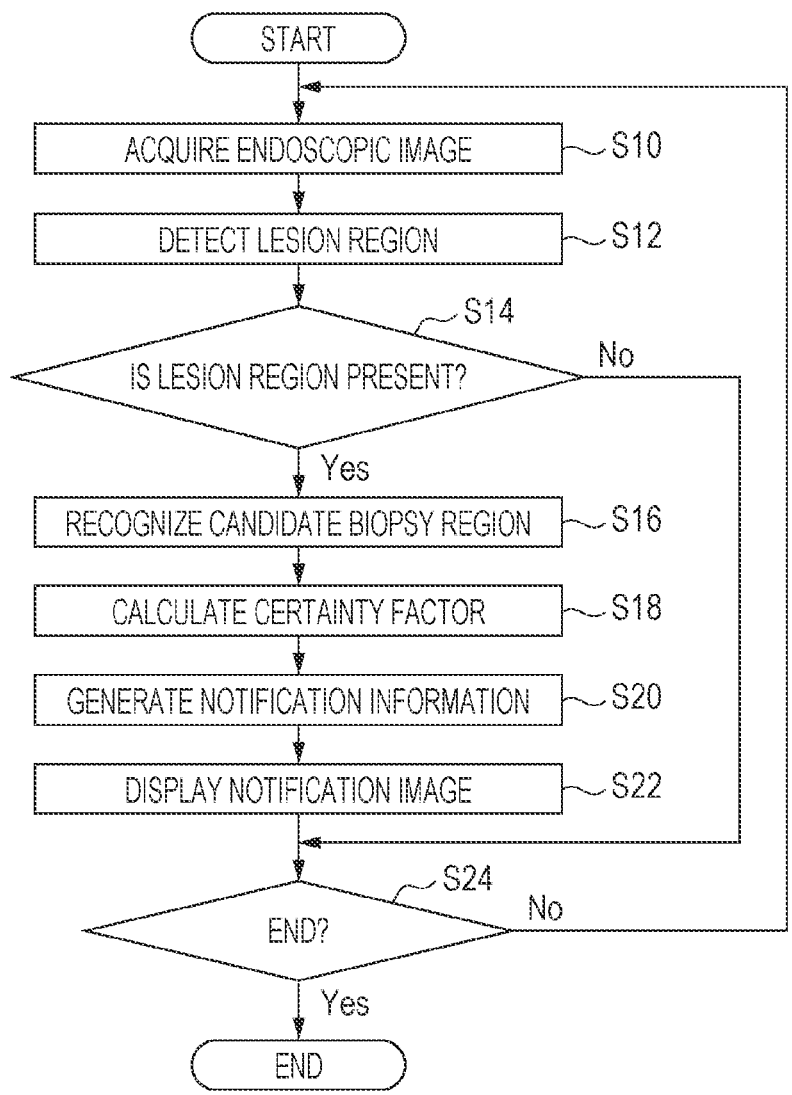
FIG. 4 is a flowchart illustrating a procedure of an image processing method according to the first embodiment.

FIG. 4 is a flowchart illustrating a procedure of an image processing method according to the first embodiment. In an endoscopic image acquisition step S10, the endoscopic image acquisition unit 222 illustrated in FIG. 3 acquires the endoscopic image 38. Endoscopic image acquisition step S10 is followed by lesion region detection step S12.

In lesion region detection step S12, the lesion region detection unit 224 detects a lesion region from each of the frame images 38B constituting the endoscopic image 38 or the still image 39. The lesion region detection unit 224 stores information on the detected lesion region. Lesion region detection step S12 is followed by lesion region determination step S14.

In lesion region determination step S14, the candidate biopsy region recognition unit 226 determines whether a lesion region has been detected in the frame image 38B or the still image 39. If the candidate biopsy region recognition unit 226 determines in lesion region determination step S14 that there is no lesion region in the frame image 38B or the still image 39 of a determination target, the determination is No. No determination is followed by end determination step S24.

On the other hand, if the candidate biopsy region recognition unit 226 determines in lesion region determination step S14 that there is a lesion region in the frame image 38B or the still image 39 of a determination target, the determination is Yes. Yes determination is followed by candidate biopsy region recognition step S16.

In candidate biopsy region recognition step S16, the candidate biopsy region recognition unit 226 recognizes a candidate biopsy region for the lesion region. Candidate biopsy region recognition step S16 is followed by certainty factor calculation step S18.

In certainty factor calculation step S18, the certainty factor calculation unit 228 calculates the biopsy certainty factor for the candidate biopsy region detected in the candidate biopsy region recognition step S16. Certainly factor calculation step S18 is followed by notification information generation step S20.

In notification information generation step S20, the notification information generation unit 230 generates a notification image to be displayed so as to be superimposed on an endoscopic image as notification information based on the biopsy certainty factor generated in certainty factor calculation step S18. The notification information generation unit 230 stores the notification image in the notification information storage unit 232. Notification information generation step S20 is followed by notification image display step S22.

In notification image display step S22, the notification information generation unit 230 transmits a video signal representing the notification image to the display apparatus 400 via the video output unit 206. The display apparatus 400 displays the notification image so as to be superimposed on the endoscopic image 38. Notification image display step S22 is followed by end determination step S24.

In end determination step S24, the endoscopic image acquisition unit 222 determines whether acquisition of the endoscopic image has ended. If the last frame image 38B of the endoscopic image 38 has been acquired, the endoscopic image acquisition unit 222 may end the acquisition of the endoscopic image. The endoscopic image acquisition unit 222 may end the acquisition of the endoscopic image if a certain period has elapsed from the acquisition of a given endoscopic image.

If the endoscopic image acquisition unit 222 determines in end determination step S24 that the acquisition of the endoscopic image has not ended, the determination is No. No determination is followed by endoscopic image acquisition step S10, and the respective steps from endoscopic image acquisition step S10 to end determination step S24 are repeatedly performed until Yes determination is made in end determination step S24.

On the other hand, if the endoscopic image acquisition unit 222 determines in end determination step S24 that the acquisition of the endoscopic image has ended, the determination is Yes. In a case of Yes determination, the processor device 240 ends the image processing method.

Specific Examples of Notification Image

Figure 5:
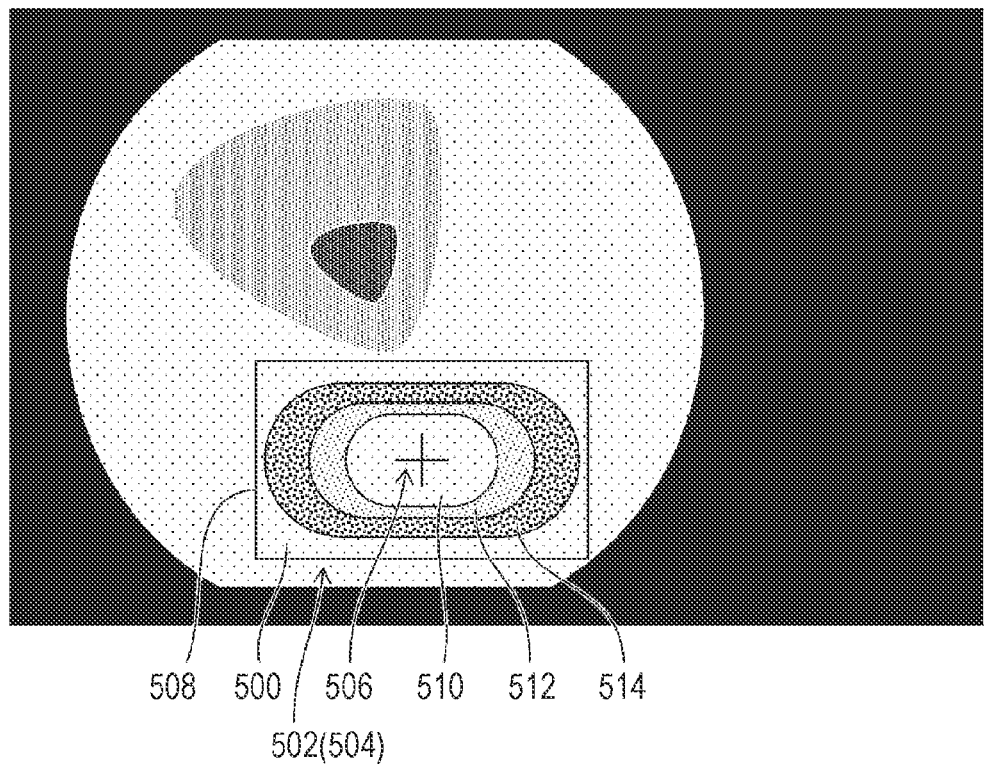
FIG. 5 is a schematic diagram of a notification image according to a first example.

FIG. 5 is a schematic diagram of a notification image according to a first example. FIG. 5 schematically illustrates a given frame image 38B constituting the endoscopic image 38 acquired when an endoscopic examination of a large intestine is performed. The same applies to FIGS. 6 and 9.

In the endoscopic image 38 illustrated in FIG. 5, a notification image 502 is displayed so as to be superimposed on a lesion region 500. In the endoscopic image 38, a center position 506 of the lesion region 500 and a bounding box 508 surrounding the outer periphery of the lesion region 500 are displayed.

The notification image 502 illustrated in FIG. 5 has a size and a shape to cover the entirety of a candidate biopsy region 504. In the notification image 502, the degree of notification is changed depending on the biopsy certainty factor. The notification image 502 includes a first region 510, a second region 512, and a third region 514.

The first region 510 is a region in which the biopsy certainty factor is maximum, and is a region including the center position of the lesion region 500. The second region 512 is a region having a lower biopsy certainty factor than the first region 510, and is a region outside the first region 510. The third region 514 is a region having a lower biopsy certainty factor than the second region 512, and is a region outside the second region 512.

The first region 510 is a region in which the degree of notification is the lowest, and displays the notification image 502 in a manner close to that for a normal image of the endoscopic image 38. The second region 512 is a region having a higher degree of notification than the first region 510, and emphasizes the first region 510. The third region 514 is a region having a higher degree of notification than the second region 512, and emphasizes the first region 510 as in the second region 512.

That is, the notification image 502 may improve the user's visibility with respect to the candidate biopsy region 504, and may suppress the obstruction of the user's field of view with respect to a region having a relatively high biopsy certainty factor in the candidate biopsy region.

As an example of changing the degree of notification, there is an example of controlling image quality. Examples of image quality include saturation and luminance. Another example of image quality is resolution. That is, in the first region 510, the second region 512, and the third region 514 illustrated in FIG. 5, as the distance from the center position 506 of the lesion region 500 increases, the saturation may be decreased, the luminance may be decreased, or the resolution may be decreased.

In the notification image 502, a range in which the luminance or the like is changed is limited to a range that can be changed using the processor apparatus 200 illustrated in FIG. 2. That is, the degree of notification of the notification image 502 is limited to a range that can be adjusted by the user who uses the endoscope system 10. Examples of parameters that can be set by the user include luminance, saturation, tint, and white balance.

As a result, the notification image 502 is not largely different from that in the past, and is not significantly different from normal observation display of the endoscopic image 38, and thus, the user can easily observe the notification image 502.

Figure 6:
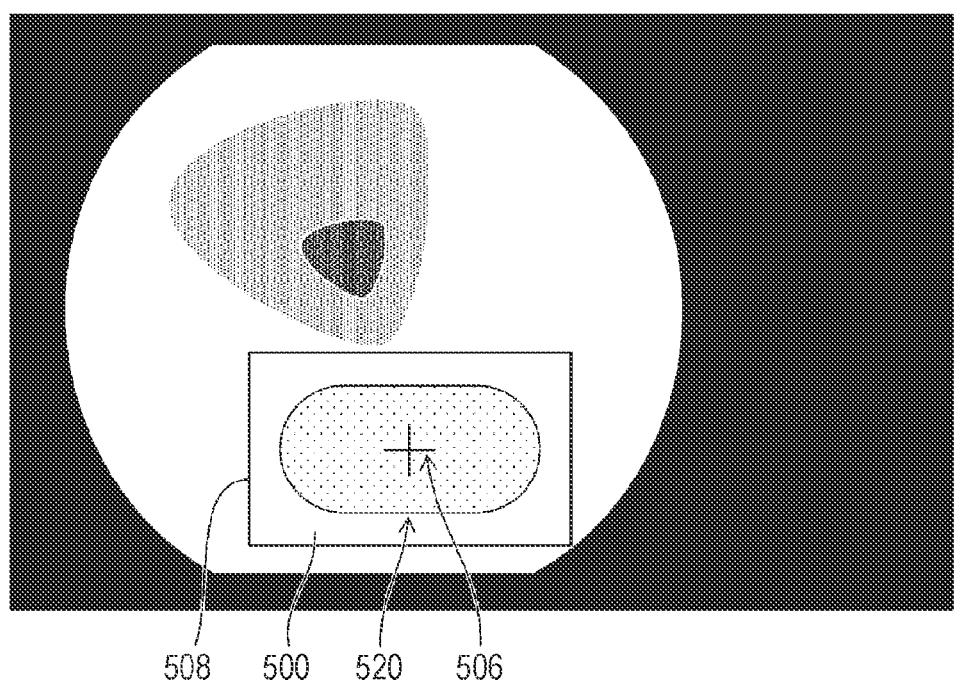
FIG. 6 is a schematic diagram of a notification image according to a second example.

FIG. 6 is a schematic diagram of a notification image according to a second example. In a notification image 520 illustrated in FIG. 6, a threshold value for the biopsy certainty factor is set, and the degree of notification is changed depending on whether the biopsy certainty factor exceeds the threshold value. The notification image 520 illustrated in FIG. 6 is composed of a region in which the biopsy certainty factor exceeds the threshold value. Accordingly, it is possible to provide the notification image 520 that allows the user to intuitively determine the biopsy region.

The notification information generation unit 230 illustrated in FIG. 3 includes a threshold value setting unit that sets a threshold value applied to the biopsy certainty factor.

The threshold value setting unit may set the threshold value based on input information of the user.

Modification of Notification Image Display

The notification image 502 may be automatically hidden at a timing at which a prescribed period has elapsed from the display start timing. The prescribed period may be fixed or may be adjustable.

That is, the processor device 240 illustrated in FIG. 3 may measure the elapsed period from the display start timing of the notification image 502, and may automatically hide the notification image 502 at a timing at which the prescribed period has elapsed from the measurement start timing.

After a certain period has elapsed from the display start timing of the notification image 502, it may be determined that the user has finished checking the biopsy region. If the notification image 502 is automatically hidden, the user is not bothered.

The notification image 502 may be hidden in response to a command signal for hiding the notification image 502. For example, a command signal for hiding the notification image 502 may be transmitted in response to an operation of a button or the like by the user, and the notification image 502 may be hidden. Note that the display control of the notification image 502 according to the modification is also applicable to the notification image 520 illustrated in FIG. 6.

Specific Example of Candidate Biopsy Region

The candidate biopsy region may be recognized based on the lesion certainty factor representing the certainty of the lesion region in the lesion region 500. For example, a region having a lesion certainty factor exceeding the prescribed threshold value may be set as a candidate biopsy region. The candidate biopsy region may be defined as a region including the center position 506 of the lesion region 500.

The candidate biopsy region may be recognized using a trained learning model. The learning model may apply CNN. CNN is an abbreviation for Convolutional Neural Network.

Specific Example of Biopsy Certainty Factor

The biopsy certainty factor is calculated for each of the pixels constituting the candidate biopsy region 504. Each of the first region 510, the second region 512, and the third region 514 illustrated in FIG. 5 represents a set of a plurality of pixels having the same biopsy certainty factor.

If the candidate biopsy region is recognized based on the lesion certainty factor, the lesion certainty factor in the candidate biopsy region may be the biopsy certainty factor.

Advantageous Effects of First Embodiment

The endoscope system and the image processing method according to the first embodiment can obtain the following advantageous effects.

[1]

The candidate biopsy region 504 is recognized for the lesion region 500, the biopsy certainty factor is calculated for the candidate biopsy region 504, the notification image 502 in which the degree of notification differs depending on the biopsy certainty factor is generated, and the notification image 502 is displayed so as to be superimposed on the endoscopic image 38. In the notification image 502, the degree of notification is reduced in the first region 510 where the biopsy certainty factor is relatively high compared to the second region 512 and the like where the biopsy certainty factor is relatively low. Accordingly, it is possible to notify the biopsy certainty factor with which the obstruction of the user's field of view is suppressed.

[2]

In the notification image 502, the image quality of the second region 512 and the third region 514 is reduced compared to the first region 510. Accordingly, the same observation state as that in the normal observation of the endoscopic image 38 is implemented in the first region 510, and the first region 510 can be emphasized.

[3]

In the notification image 502, the luminance and saturation of the second region 512 and the third region 514 are reduced compared to the first region 510. Accordingly, the same observation state as that in the normal observation of the endoscopic image 38 is implemented in the first region 510, and the first region 510 can be emphasized.

[4]

The range in which the luminance or the like differs in the notification image 502 is limited to a range that is adjustable in the endoscope system 10. Accordingly, the endoscopic image 38 on which the notification image 502 is superimposed is not significantly different from the normal display of the endoscopic image 38, and the displayed endoscopic image 38 on which the notification image 502 is displayed so as to be superimposed is easy to observe.

[5]

The notification image 502 is automatically hidden after the prescribed period has elapsed from the display start timing of the notification image 502. Accordingly, the user may be prevented from being bothered when the notification image 502 is hidden.

Endoscope System According to Second Embodiment

Figure 7:
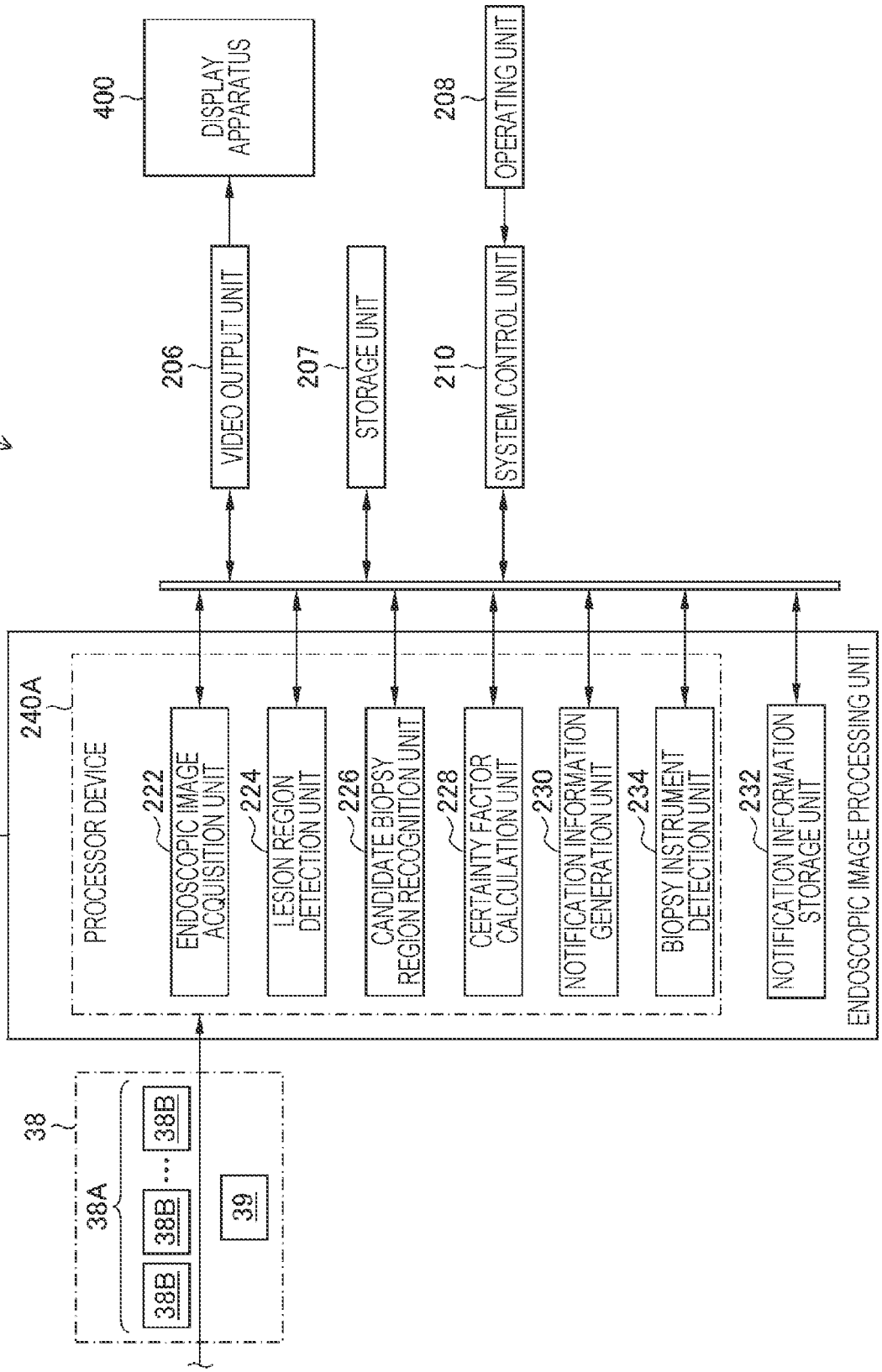
FIG. 7 is a functional block diagram of an endoscope system according to a second embodiment.

FIG. 7 is a functional block diagram of an endoscope system according to a second embodiment. In an endoscope system 10A illustrated in FIG. 7, the configuration of a processor device 240A provided in an endoscopic image processing unit 220A is different from that in the endoscope system 10 illustrated in FIG. 1 and the like.

That is, in the endoscope system 10A, a biopsy instrument detection unit 234 is provided in the processor device 240A. The biopsy instrument detection unit 234 detects whether a biopsy instrument such as forceps is included in the endoscopic image 38.

If a detection result indicating that the biopsy instrument detection unit 234 detects a biopsy instrument is obtained, the video output unit 206 stops the superimposed display of the notification image on the endoscopic image 38. If a biopsy instrument is included in the endoscopic image 38, it is determined that a user has already recognized a biopsy region. To precisely observe the biopsy region, the superimposed display of the notification image is automatically stopped if a biopsy instrument is detected.

Procedure of Image Processing Method According to Second Embodiment

Figure 8:
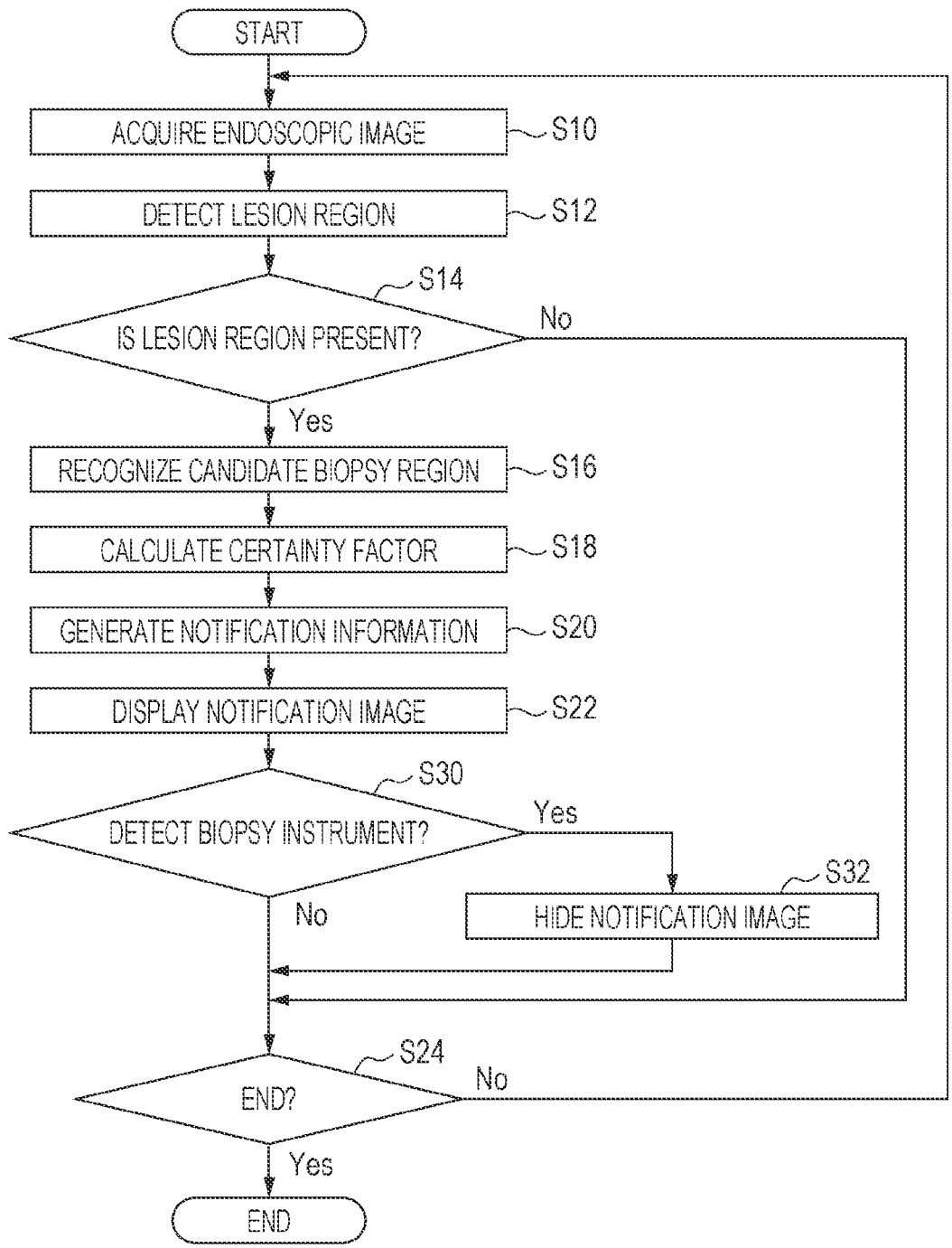
FIG. 8 is a flowchart illustrating a procedure of an image processing method according to the second embodiment.

FIG. 8 is a flowchart illustrating a procedure of an image processing method according to the second embodiment. In the flowchart illustrated in FIG. 8, biopsy instrument detection step S30 and notification image hiding step S32 are added to the flowchart illustrated in FIG. 4.

In notification image display step S22, the notification image 502 is displayed so as to be superimposed on the endoscopic image 38 on the display apparatus 400, which is followed by biopsy instrument detection step S30. In biopsy instrument detection step S30, the biopsy instrument detection unit 234 illustrated in FIG. 7 performs biopsy instrument detection from the endoscopic image 38.

If the biopsy instrument detection unit 234 detects a biopsy instrument from the endoscopic image 38 in biopsy instrument detection step S30, the determination is Yes. Yes determination is followed by notification image hiding step S32. On the other hand, if the biopsy instrument detection unit 234 does not detect a biopsy instrument from the endoscopic image 38 in biopsy instrument detection step S30, the determination is No. No determination is followed by end determination step S24.

In notification image hiding step S32, the notification information generation unit 230 hides the notification image 502 displayed and superimposed on the endoscopic image 38 via the video output unit 206. Notification image hiding step S32, in which the notification image 502 is hidden, is followed by end determination step S24.

Specific Examples of Notification Image

FIG. 9 is a schematic diagram of transition of a notification image. Reference numeral 600 illustrated in FIG. 9 schematically illustrates the endoscopic image 38 when a biopsy instrument 602 is detected. Reference numeral 610 schematically illustrates the endoscopic image 38 in which the notification image 502 is hidden. In the notification image 502 illustrated in the schematic diagram 600 of the endoscopic image, the illustration of the first region 510 and the like illustrated in FIG. 5 is omitted.

In the endoscopic image 38 illustrated as the schematic diagram 610 of the endoscopic image, the bounding box for emphasizing the lesion region 500 is hidden, but the bounding box may be displayed. The biopsy instrument 602 illustrated in FIG. 9 is an example of a treatment tool.

Modification of Second Embodiment

During biopsy, there may be a case where it is desired to recognize the position of a candidate biopsy region. Therefore, if the biopsy instrument 602 illustrated in FIG. 9 is detected, the display of the notification image 502 may be continued, and when the biopsy instrument 602 is not detected, it may be determined that the biopsy has ended, and the notification image 502 may be automatically hidden.

In the image processing method according to the modification, a biopsy instrument non-detection step is added between biopsy instrument detection step S30 and notification image hiding step S32 in the flowchart illustrated in FIG. 8. In the biopsy instrument non-detection step, the biopsy instrument detection unit 234 illustrated in FIG. 7 determines whether the biopsy instrument detected in biopsy instrument detection step S30 is absent.

If the biopsy instrument detection unit 234 detects the biopsy instrument in biopsy instrument non-detection step, the determination is No. In a case of No determination, the biopsy instrument non-detection step is repeatedly performed until Yes determination is made in the biopsy instrument non-detection step.

On the other hand, if the biopsy instrument detection unit 234 determines that the biopsy instrument is absent in the biopsy instrument non-detection step, the determination is Yes. Yes determination is followed by notification image hiding step S32. After notification image hiding step S32 is performed, end determination step S24 is performed.

Advantageous Effects of Second Embodiment

The endoscope system and the image processing method according to the second embodiment can obtain the following advantageous effects.

[1]

If the biopsy instrument 602 is detected from the endoscopic image 38, the notification image 502 is hidden. Accordingly, the obstruction of the user's field of view of the notification image 502 may be suppressed at the time of biopsy.

[2]

If the biopsy instrument 602 is detected from the endoscopic image 38 and then the biopsy instrument 602 is not detected from the endoscopic image 38, the notification image 502 is hidden. Accordingly, at the time of biopsy, the candidate biopsy region may be recognized, and the obstruction of the user's field of view of the notification image 502 may be suppressed.

Hardware Configuration of Processing Units

Various processor devices may be applied to the various processing units illustrated in FIGS. 2, 3, 7, and the like. Note that the processing unit may be referred to as a processing section. The various processing devices include a CPU (Central Processing Unit), a PLD (Programmable Logic Device), an ASIC (Application Specific Integrated Circuit), and the like.

The CPU is a general-purpose processor device that executes programs and functions as various processing units. The PLD is a processor device whose circuit configuration can be changed after manufacture. An example of the PLD is an FPGA (Field Programmable Gate Array). The ASIC is a dedicated electric circuit having a circuit configuration specifically designed to execute a specific process.

One processing unit may be configured by one of these various processor devices, or may be configured by two or more processor devices of the same type or different types. For example, one processing unit may be configured using a plurality of FPGAs or the like. One processing unit may be configured by combining one or more FPGAs and one or more CPUs.

In addition, a plurality of processing units may be configured using one processor device. As an example of configuring a plurality of processing units using one processor device, there is a form in which one processor device is configured by combining one or more CPUs and software, and the one processor device functions as a plurality of processing units. Such a form is represented by a computer such as a client terminal apparatus or a server apparatus.

As another configuration example, there is a form using a processor device that implements the functions of the entire system including a plurality of processing units by using one IC chip. Such a form is represented by a system on chip or the like. Note that IC is an abbreviation for Integrated Circuit. A system on chip may also be referred to as an SoC using an abbreviation for System On Chip.

In this manner, various processing units are constituted by one or more of the above various processor devices in terms of hardware configuration. More specifically, the hardware configuration of various processor devices is electric circuitry constituted by combining circuit elements such as semiconductor elements.

Modifications of Endoscope System

Modifications of Illumination Light

An example of a medical image that can be acquired using the endoscope system 10 illustrated in FIG. 1 is a normal-light image obtained by irradiation with light in the white range or light in a plurality of wavelength ranges as the light in the white range.

Another example of the medical image that can be acquired using the endoscope system 10 according to the first embodiment is an image obtained by irradiation with light in a specific wavelength range. The specific wavelength range can be narrower than the white range. The following modifications are applicable.

First Modification

A first example of the specific wavelength range is the blue range or the green range in the visible range. The wavelength range of the first example includes a wavelength range of not less than 390 nanometers and not more than 450 nanometers, or not less than 530 nanometers and not more than 550 nanometers, and the light of the first example has a peak wavelength in the wavelength range of not less than 390 nanometers and not more than 450 nanometers, or not less than 530 nanometers and not more than 550 nanometers.

Second Modification

A second example of the specific wavelength range is the red range in the visible range. The wavelength range of the second example includes a wavelength range of not less than 585 nanometers and not more than 615 nanometers, or not less than 610 nanometers and not more than 730 nanometers, and the light of the second example has a peak wavelength in the wavelength range of not less than 585 nanometers and not more than 615 nanometers, or not less than 610 nanometers and not more than 730 nanometers.

Third Modification

A third example of the specific wavelength range includes a wavelength range in which oxidized hemoglobin and reduced hemoglobin have different absorption coefficients, and light of the third example has a peak wavelength in the wavelength range in which oxidized hemoglobin and reduced hemoglobin have different absorption coefficients. The wavelength range of the third example includes a wavelength range of 400±10 nanometers, 440±10 nanometers, 470±10 nanometers, or not less than 600 nanometers and not more than 750 nanometers, and the light of the third example has a peak wavelength in the wavelength range of 400±10 nanometers, 440±10 nanometers, 470±10 nanometers, or not less than 600 nanometers and not more than 750 nanometers.

Fourth Modification

A fourth example of the specific wavelength range is a wavelength range of excitation light that is used for observation of fluorescence emitted by a fluorescent substance in a living body and excites the fluorescent substance. An example is a wavelength range of not less than 390 nanometers and not more than 470 nanometers. Note that the observation of fluorescence may be referred to as fluorescence observation.

Fifth Modification

A fifth example of the specific wavelength range is the wavelength range of infrared light. The wavelength range of the fifth example includes a wavelength range of not less than 790 nanometers and not more than 820 nanometers, or not less than 905 nanometers and not more than 970 nanometers, and the light of the fifth example has a peak wavelength in the wavelength range of not less than 790 nanometers and not more than 820 nanometers, or not less than 905 nanometers and not more than 970 nanometers.

Generation Example of Special-Light Image

The processor apparatus 200 may generate a special-light image having information on the specific wavelength range, based on a normal-light image obtained by image capturing using the white light. Note that the generation herein includes acquisition. In this case, the processor apparatus 200 functions as a special-light image acquisition unit. Then, the processor apparatus 200 obtains a signal of the specific wavelength range by performing calculation based on color information of red, green, and blue, or cyan, magenta, and yellow, included in the normal-light image.

Note that cyan, magenta, and yellow may be expressed as CMY using the initials of Cyan, Magenta and Yellow.

Generation Example of Feature-Quantity Image

As a medical image, a feature-quantity image may be generated using a calculation based on at least one of a normal-light image obtained by irradiation with light in the white range or light in a plurality of wavelength ranges as light in the white range, or a special-light image obtained by irradiation with light in the specific wavelength range.

Combination of Embodiments, Modifications, Etc

The components described in the above-described embodiments can be used in appropriate combination, and some components can be replaced.

Example of Application to Image Processing System

The endoscopic image processing unit 220 illustrated in FIG. 3 and the endoscopic image processing unit 220A illustrated in FIG. 7 may be components of an image processing apparatus including one or more processors and one or more memories. Such an image processing apparatus may configure a medical image processing system that displays a notification image so as to be superimposed on not only an endoscopic image but also a medical image other than an endoscopic image acquired from a modality other than the endoscope system, such as a CT image, an MRI image, and an ultrasound image. Note that the medical image processing system represents a concept including medical image processing.

Here, the medical image may include the meaning of a medical image. Note that CT is an abbreviation for Computed Tomography. MRI is an abbreviation for Magnetic Resonance Imaging.

Example of Application to Program

The endoscope system and the image processing method described above can be configured as a program that uses a computer to implement functions corresponding to the respective units of the endoscopic image processing unit 220 and the respective steps of the image processing method. Examples of the functions implemented by using a computer include a function of acquiring a medical image, a function of detecting a lesion region from the medical image, a function of recognizing a candidate biopsy region from the lesion region, a function of calculating a biopsy certainty factor for the candidate biopsy region, a function of generating a notification image in which a degree of notification is changed depending on the biopsy certainty factor, and a function of transmitting a signal for displaying the notification image so as to be superimposed on an endoscopic image.

It is possible to store a program for causing a computer to implement the above-described various functions in a computer-readable information storage medium, which is a tangible non-transitory information storage medium, and to provide the program through the information storage medium.

Instead of providing the program that is stored in the non-transitory information storage medium, a program signal can be provided via a communication network.

In the embodiments of the present invention described above, the constituent elements can be changed, added, or deleted as appropriate without departing from the gist of the present invention. The present invention is not limited to the embodiments described above, and various modifications can be made by a person having ordinary knowledge in the art within the technical thought of the present invention.

REFERENCE SIGNS LIST

10 endoscope system
10A endoscope system
38 endoscopic image
38A moving image
38B frame image
39 still image
100 endoscope main body
102 hand operating unit
104 insertion unit
106 universal cable
108 light guide connector
112 soft part
114 bending part
116 tip rigid part
116A distal-end-side end surface
123 illumination unit
123A illumination lens
123B illumination lens
126 forceps port
130 imaging unit
132 imaging lens
134 imaging device
136 driving circuit
138 analog front end
141 air/water supply button
142 suction button
143 function button
144 imaging button
170 light guide
200 processor apparatus
202 imaging signal acquisition unit
204 imaging signal processing unit
205 communication control unit
206 video output unit
207 storage unit
208 operating unit
209 audio processing unit
209A speaker
210 system control unit
211 ROM
212 RAM
220 endoscopic image processing unit
220A endoscopic image processing unit
222 endoscopic image acquisition unit
224 lesion region detection unit
226 candidate biopsy region recognition unit
228 certainty factor calculation unit
230 notification information generation unit
232 notification information storage unit
240 processor device
240A processor device
300 light source device
310 light source
310B blue light source 310G green light source
310R red light source
330 aperture diaphragm
340 condenser lens
350 light source control unit
400 display apparatus
500 lesion region
502 notification image
504 candidate biopsy region
506 center position
508 bounding box
510 first region
512 second region
514 third region
520 notification image
600 schematic diagram of endoscopic image
602 biopsy instrument
610 schematic diagram of endoscopic image
S10 to S32 image processing method step

What is claimed is:

1. An image processing system comprising
one or more processors configured to:
acquire a medical image;
detect a region of interest from the medical image;
calculate a biopsy certainty factor for the region of interest, the biopsy certainty factor representing certainty of a biopsy region that is a biopsy target;
generate a notification image in which a degree of notification differs depending on the calculated biopsy certainty factor, the notification image being to be displayed so as to be superimposed on the medical image;
transmit a display signal representing the notification image to a display apparatus;
detect whether a biopsy instrument is included in the medical image; and
stop transmission of the display signal representing the notification image if a detection result indicating that the biopsy instrument is included in the medical image is obtained.

2. The image processing system according to claim 1, wherein the one or more processors are configured to
set a threshold value for the biopsy certainty factor, and
cause a biopsy certainty factor exceeding the threshold value to be displayed as the notification image.

3. The image processing system according to claim 1, wherein the one or more processors are configured to generate the notification image in which an image quality of the notification image differs depending on the calculated biopsy certainty factor.

4. The image processing system according to claim 3, wherein the one or more processors are configured to generate the notification image in which the image quality of a region in which the biopsy certainty factor is relatively small is reduced compared to a region in which the biopsy certainty factor is relatively large.

5. The image processing system according to claim 3, wherein the one or more processors are configured to generate the notification image in which a saturation of the notification image differs depending on the calculated biopsy certainty factor.

6. The image processing system according to claim 5, wherein the one or more processors are configured to generate the notification image in which the saturation of a region in which the biopsy certainty factor is relatively small is reduced compared to a region in which the biopsy certainty factor is relatively large.

7. The image processing system according to claim 3, wherein the one or more processors are configured to generate the notification image in which a luminance of the notification image differs depending on the calculated biopsy certainty factor.

8. The image processing system according to claim 7, wherein the one or more processors are configured to generate the notification image in which the luminance of a region in which the biopsy certainty factor is relatively small is reduced compared to a region in which the biopsy certainty factor is relatively large.

9. The image processing system according to claim 1, wherein the one or more processors are configured to
measure an elapsed period from a display start timing of the notification image, and
stop transmission of the display signal representing the notification image if the elapsed period from the display start timing of the notification image exceeds a prescribed period.

10. The image processing system according to claim 1, wherein the one or more processors are configured to
detect whether a biopsy has been performed, and
stop transmission of the display signal representing the notification image if a detection result indicating that the biopsy has been performed is obtained.

11. The image processing system according to claim 1, wherein the one or more processors are configured to
calculate a lesion certainty factor for the region of interest, the lesion certainty factor representing certainty of a lesion, and
calculate the biopsy certainty factor for the region of interest in which the lesion certainty factor exceeds a prescribed threshold value.

12. A processor apparatus for controlling an endoscope, comprising
one or more processors configured to:
acquire an endoscopic image from the endoscope;
detect a region of interest from the endoscopic image;
calculate a biopsy certainty factor for the region of interest, the biopsy certainty factor representing certainty of a biopsy region that is a biopsy target;
generate a notification image in which a degree of notification differs depending on the calculated biopsy certainty factor, the notification image being to be displayed so as to be superimposed on the endoscopic image;
transmit a display signal representing the notification image to a display apparatus;
detect whether a biopsy instrument is included in the endoscopic image; and
stop transmission of the display signal representing the notification image if a detection result indicating that the biopsy instrument is included in the endoscopic image is obtained.

13. An endoscope system comprising:
an endoscope;
a processor apparatus for controlling the endoscope; and
one or more processors configured to:
acquire an endoscopic image from the endoscope;
detect a region of interest from the endoscopic image;
calculate a biopsy certainty factor for the region of interest, the biopsy certainty factor representing certainty of a biopsy region that is a biopsy target;
generate a notification image in which a degree of notification differs depending on the calculated biopsy certainty factor, the notification image being to be displayed so as to be superimposed on the endoscopic image;

transmit a display signal representing the notification image to a display apparatus;

detect whether a biopsy instrument is included in the endoscopic image; and stop transmission of the display signal representing the notification image if a detection result indicating that the biopsy instrument is included in the endoscopic image is obtained.

14. An image processing method comprising:

acquiring a medical image;

detecting a region of interest from the medical image;

calculating a biopsy certainty factor for the region of interest, the biopsy certainty factor representing certainty of a biopsy region that is a biopsy target;

generating a notification image in which a degree of notification differs depending on the calculated biopsy certainty factor, the notification image being to be displayed so as to be superimposed on the medical image;

transmitting a display signal representing the notification image to a display apparatus;

detecting whether a biopsy instrument is included in the medical image; and stopping transmission of the display signal representing the notification image if a detection result indicating that the biopsy instrument is included in the medical image is obtained.

15. A non-transitory, computer-readable tangible recording medium which records thereon a program for causing, when read by a computer, the computer to implement:

a function of acquiring a medical image;

a function of detecting a region of interest from the medical image;

a function of calculating a biopsy certainty factor for the region of interest, the biopsy certainty factor representing certainty of a biopsy region that is a biopsy target;

a function of generating a notification image in which a degree of notification differs depending on the calculated biopsy certainty factor, the notification image being to be displayed so as to be superimposed on the medical image;

a function of transmitting a display signal representing the notification image to a display apparatus;

a function of detecting whether a biopsy instrument is included in the medical image; and a function of stopping transmission of the display signal representing the notification image if a detection result indicating that the biopsy instrument is included in the medical image is obtained.

* * * * *